(12) United States Patent
Hata et al.

(10) Patent No.: US 9,192,722 B2
(45) Date of Patent: Nov. 24, 2015

(54) PHARMACEUTICAL INJECTION DEVICE

(75) Inventors: Shinsuke Hata, Ehime (JP); Tatsuya Kawabata, Ehime (JP); Seiji Kikuchi, Ehime (JP); Tsuguhiro Kondoh, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 22 days.

(21) Appl. No.: 14/342,668

(22) PCT Filed: Aug. 6, 2012

(86) PCT No.: PCT/JP2012/004990
§ 371 (c)(1),
(2), (4) Date: Mar. 4, 2014

(87) PCT Pub. No.: WO2013/038593
PCT Pub. Date: Mar. 21, 2013

(65) Prior Publication Data
US 2014/0207058 A1    Jul. 24, 2014

(30) Foreign Application Priority Data
Sep. 12, 2011  (JP) ................. 2011-198098

(51) Int. Cl.
*A61M 5/20* (2006.01)
*A61M 5/24* (2006.01)
*A61M 5/31* (2006.01)

(52) U.S. Cl.
CPC .............. *A61M 5/2066* (2013.01); *A61M 5/20* (2013.01); *A61M 5/2448* (2013.01); *A61M 5/3146* (2013.01); *A61M 2005/206* (2013.01); *A61M 2205/215* (2013.01); *A61M 2205/50* (2013.01)

(58) Field of Classification Search
CPC ... A61M 5/2066; A61M 5/2448; A61M 5/20; A61M 2005/215; A61M 2205/50; A61M 2005/206; A61M 5/284; A61M 5/285; A61M 5/315; A61M 5/31596; A61M 5/3202
USPC ............ 128/DIG. 1, 12, 13; 604/92, 131, 151
See application file for complete search history.

(56) References Cited

U.S. PATENT DOCUMENTS 6,645,179 B1    11/2003  Ishikawa et al.
6,869,413 B2 *   3/2005  Langley et al. ................. 604/65
(Continued)

FOREIGN PATENT DOCUMENTS

JP    11-513586 A    11/1999
JP    2001-17545 A    1/2001
(Continued)

OTHER PUBLICATIONS

International Search Report for Application No. PCT/JP2012/004990 dated Nov. 6, 2012.

*Primary Examiner* — Kami A Bosworth
*Assistant Examiner* — Hamza Darb
(74) *Attorney, Agent, or Firm* — Pearne & Gordon LLP

(57) ABSTRACT

This pharmaceutical injection device comprises a main body case (2) having an injection needle extension/retraction opening (1); a pharmaceutical syringe mounting portion (3) provided inside the main body case (2); a piston (5) capable of moving relative to the pharmaceutical syringe mounting portion (3); a drive mechanism (6) for the piston (5); a controller (7) that is electrically connected to the drive mechanism (6); and an orientation sensor (8) that is electrically connected to the controller (7). The controller (7) controls the speed of the piston (5) in order to reduce liquid leakage during pharmaceutical mixing.

3 Claims, 13 Drawing Sheets

(56) References Cited

U.S. PATENT DOCUMENTS

| | | |
|---|---|---|
| 8,298,171 B2 | 10/2012 | Ishikawa et al. |
| 8,679,055 B2 | 3/2014 | Ishikawa et al. |
| 2005/0209569 A1 | 9/2005 | Ishikawa et al. |
| 2011/0301534 A1* | 12/2011 | Renz et al. .............. 604/82 |
| 2012/0310157 A1 | 12/2012 | Ishikawa et al. |
| 2012/0323176 A1 | 12/2012 | Watanabe et al. |
| 2014/0148760 A1 | 5/2014 | Ishikawa et al. |

FOREIGN PATENT DOCUMENTS

| | | |
|---|---|---|
| JP | 2004-516107 A | 6/2004 |
| JP | 2010-17417 A | 1/2010 |
| JP | 2010-279793 A | 12/2010 |
| WO | 97/14459 A1 | 4/1997 |
| WO | 02/051476 A1 | 7/2002 |
| WO | WO 2010091774 A1 * | 8/2010 |
| WO | 2011/108225 A1 | 9/2011 |

* cited by examiner

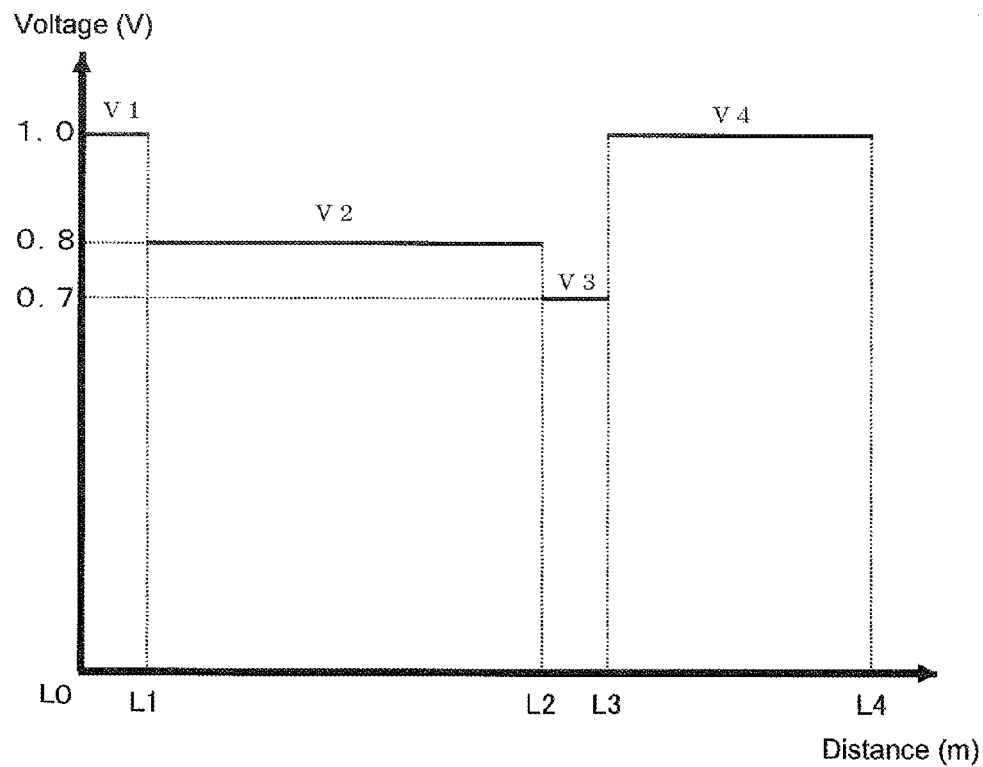

L0: initial position of separation gasket rear end
L1: position when separation gasket rear end touches the bypass
(at the start of mixing)
L2: position when separation gasket rear end touches the push-in gasket
(at the end of mixing)
L3: position of separation gasket distal end after air venting
L4: position of separation gasket distal end after completion of
pharmaceutical injection

FIG. 8

PHARMACEUTICAL INJECTION DEVICE

TECHNICAL FIELD

The present invention relates to a pharmaceutical injection device.

BACKGROUND ART

A conventional pharmaceutical injection device comprises a main body case having an injection needle extension/retraction opening; a pharmaceutical syringe mounting portion provided inside the main body case; a pharmaceutical syringe mounted to the pharmaceutical syringe mounting portion; a piston capable of moving relative to the pharmaceutical syringe mounting portion; a drive mechanism for driving the piston; a controller that is electrically connected to the drive mechanism; and an orientation sensor that is electrically connected to the controller.

Also, the pharmaceutical syringe has a cylinder, a distal end gasket provided on the distal end side within the cylinder, a push-in gasket provided on the rear end side within the cylinder, a separation gasket provided in the middle within the cylinder, a solid pharmaceutical housed in the cylinder between the distal end gasket and the separation gasket, a liquid pharmaceutical housed in the cylinder between the push-in gasket and the separation gasket, and a bypass that sticks out in the outer peripheral direction of the cylinder at a portion of the cylinder between the distal end gasket and the separation gasket (see Patent Literature 1, for example).

The controller uses the drive mechanism to push the push-in gasket to the distal end gasket side with the piston after detection of the orientation position by the orientation sensor (see Patent Literature 2, for example).

CITATION LIST

Patent Literature

Patent Literature 1: Japanese Laid-Open Patent Application 2001-17545
Patent Literature 2: Japanese Unexamined Patent Application Publication (Translation of PCT Application) No H11-513586

SUMMARY

Technical Problem

However, the following problems were encountered with the conventional pharmaceutical injection devices discussed above.

Specifically, with the pharmaceutical injection devices discussed in the above-mentioned publications, there was the risk that some of the liquid pharmaceutical would squirt out from the injection needle mounted to the distal end gasket of the cylinder during mixing of the liquid pharmaceutical and the solid pharmaceutical.

This is because with a conventional configuration, after the controller has used the orientation sensor to detect the orientation position, the drive mechanism uses the piston to push the push-in gasket to the distal end gasket side, but the rate at which the push-in gasket is pushed in by the piston remains constant.

Therefore, once the rear end of the separation gasket reaches the bypass, the liquid pharmaceutical gushes to the solid pharmaceutical side via the bypass, and since the pressure also rises on this solid pharmaceutical side, there is the risk that some of the liquid pharmaceutical will squirt out of the injection needle mounted to the distal end gasket of the cylinder.

It is an object of the present invention to provide a pharmaceutical injection device with which there is less liquid leakage from the distal end of the injection needle, even during pharmaceutical mixing, and with which pharmaceutical mixing can be performed favorably.

Solution to Problem

To achieve the stated object, the present invention comprises a main body case, a pharmaceutical syringe mounting portion, a piston, a drive mechanism, a controller, and an orientation sensor. The main body case has an opening from which an injection needle retractably protrudes. The pharmaceutical syringe mounting portion is provided within the main body case, and a pharmaceutical syringe is removably mounted thereto. The piston is provided movably with respect to the pharmaceutical syringe. The drive mechanism drives the piston. The controller is electrically connected to the drive mechanism. The orientation sensor is electrically connected to the controller. The pharmaceutical syringe has a cylinder, a distal end gasket, a push-in gasket, a separation gasket, a liquid pharmaceutical, a liquid pharmaceutical, and a bypass. The distal end gasket is provided on the distal end side within the cylinder. The push-in gasket is provided on the rear end side within the cylinder. The separation gasket is provided in the middle within the cylinder. The solid pharmaceutical is housed in the cylinder between the distal end gasket and the separation gasket. The liquid pharmaceutical is housed in the cylinder between the push-in gasket and the separation gasket. The bypass sticks out in the outer peripheral direction of the cylinder at a portion of the cylinder between the distal end gasket and the separation gasket. The controller uses the drive mechanism to push the push-in gasket to the distal end gasket side with the piston after detection of the orientation position by the orientation sensor. The rate at which the push-in gasket is pushed in by the piston is set so that if we let V1 be the push-in rate until the separation gasket reaches the bypass, V2 be the push-in rate at the point when the separation gasket goes through the bypass, V3 be the push-in rate at the point when air is vented after the separation gasket has gone through the bypass, and V4 be the push-in rate at the point when a pharmaceutical is injected after air venting, the push-in rate V2 will be lower than the push-in rate V1.

Advantageous Effects

With the pharmaceutical injection device pertaining to the present invention, since liquid leakage can be reduced during pharmaceutical mixing, the operation of mixing the pharmaceuticals can be carried out properly. Specifically, with the present invention, since the push-in rate V2 is set to be lower than the push-in rate V1, the liquid pharmaceutical will flow through the bypass to the solid pharmaceutical side more gently, which reduces liquid leakage from the distal end of the injection needle during pharmaceutical mixing.

BRIEF DESCRIPTION OF DRAWINGS

FIG. 8 is a graph of the piston push-in rate and position of the separation gasket of the pharmaceutical injection device in FIG. 1;

DESCRIPTION OF EMBODIMENTS

An embodiment of the present invention will now be described through reference to the appended drawings.

Embodiment 1

Figure 1:
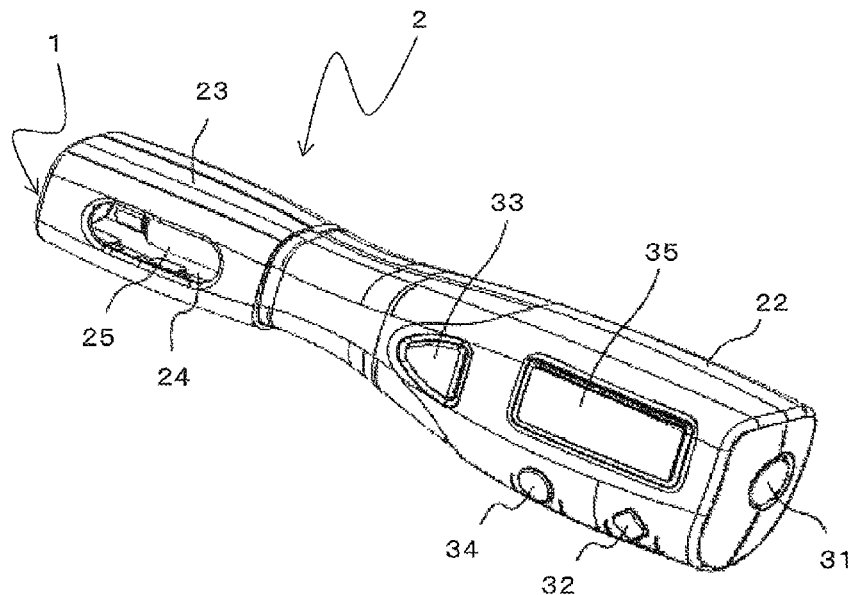
FIG. 1 is an oblique view of the pharmaceutical injection device pertaining to an embodiment of the present invention.
Figure 2:
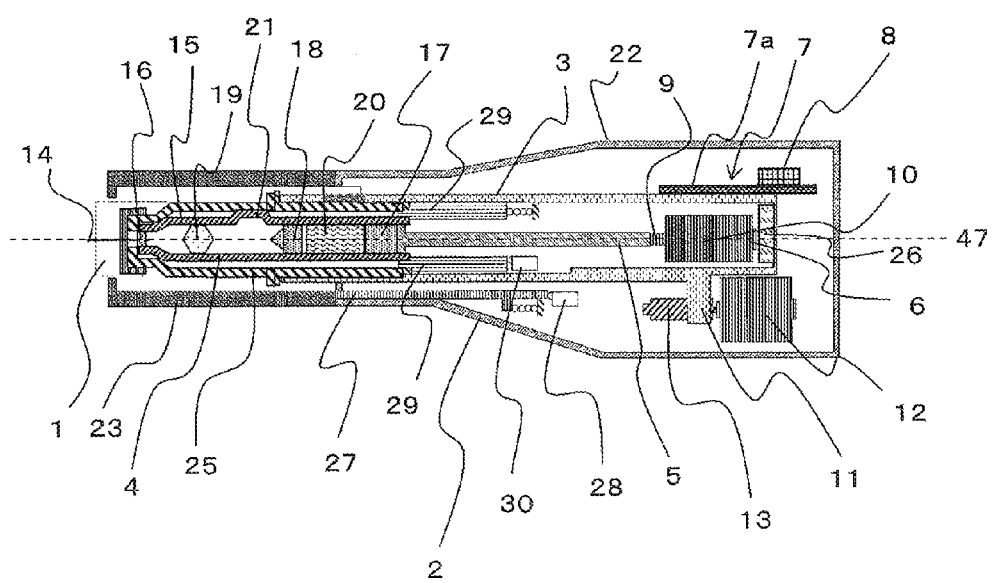
FIG. 2 is a cross section of the pharmaceutical injection device in FIG. 1.

As shown in FIGS. 1 and 2, the pharmaceutical injection device in this embodiment comprises a substantially cylindrical main body case 2, a pharmaceutical syringe mounting portion 3, a pharmaceutical syringe 4, a piston 5, a drive mechanism 6, a controller 7, and an orientation sensor 8. The main body case 2 has an injection needle extension/retraction opening 1 on the distal end side. The pharmaceutical syringe mounting portion 3 is provided within the main body case 2. The pharmaceutical syringe 4 is mounted within the pharmaceutical syringe mounting portion 3. The piston 5 is capable of moving relative to the pharmaceutical syringe 4. The drive mechanism 6 drives the piston 5. The controller 7 is electrically connected to the drive mechanism 6. The orientation sensor 8 is electrically connected to the controller 7.

The orientation sensor 8 is mounted on a substrate 7a having the controller 7. The substrate 7a is installed along the movement axis 47 of the piston 5, and parallel to the drive direction of the piston, which allows the orientation of the pharmaceutical injection device to be properly detected.

The drive mechanism 6 is made up of a bolt 9 inserted into the rear end opening of the piston 5, and a piston drive motor 10 for driving the bolt 9. Specifically, when the piston drive motor 10 is rotated in one direction, the rotation of the bolt 9 pushes the piston 5 out in the direction of the injection needle extension/retraction opening 1. Conversely, when the piston drive motor 10 is rotated the other way, the piston 5 is pulled back in the direction of the piston drive motor 10.

The piston drive motor 10 and the piston 5 are disposed along with the pharmaceutical syringe 4 within the pharmaceutical syringe mounting portion 3. Female threads 11 are provided at the outward side of the rear end of the pharmaceutical syringe mounting portion 3. A bolt 13 of a needle insertion/retraction drive motor 12 meshes with the female thread 11. When the needle insertion/retraction drive motor 12 is driven, the meshing of the female thread 11 and the bolt 13 causes the pharmaceutical syringe mounting portion 3 to move back and forth with respect to the injection needle extension/retraction opening 1. This allows an injection needle 14 provided on the distal end side of the pharmaceutical syringe 4 to be extended and retracted through the injection needle extension/retraction opening 1.

Figure 9A:
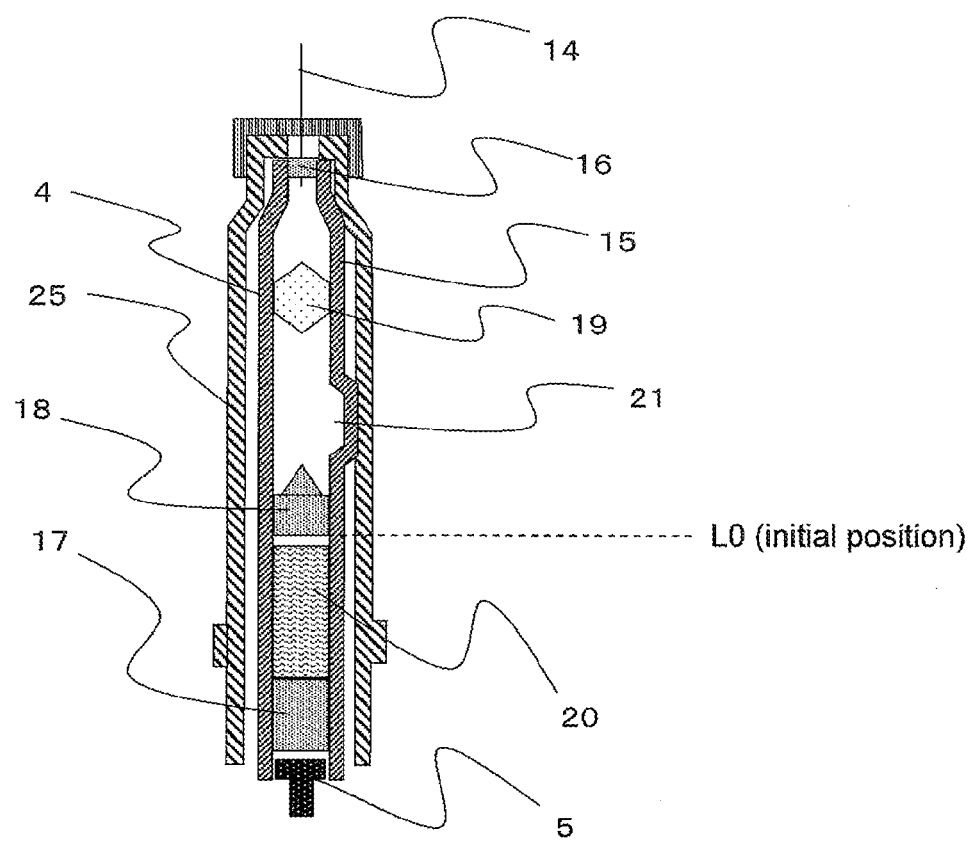
FIG. 9A is a syringe cross section of the operating state of the piston in the pharmaceutical injection device in FIG. 1.

As shown in FIG. 9A, the pharmaceutical syringe 4 has a cylinder 15, a distal end gasket 16, a push-in gasket 17, a separation gasket 18, a solid pharmaceutical 19, a liquid pharmaceutical 20, and a bypass 21. The distal end gasket 16 is provided on the distal end side within the cylinder 15. The push-in gasket 17 is provided on the rear end side within the cylinder 15. The separation gasket 18 is provided in the middle within the cylinder 15. The solid pharmaceutical 19 is housed in the cylinder 15 between the distal end gasket 16 and the separation gasket 18. The liquid pharmaceutical 20 is housed in the cylinder 15 between the push-in gasket 17 and the separation gasket 18. The bypass 21 protrudes in the outer peripheral direction of the cylinder 15 at the portion of the cylinder 15 between the distal end gasket 16 and the separation gasket 18.

The controller 7 uses the drive mechanism 6 to push the push-in gasket 17 with the piston 5 to the distal end gasket 16 side after the detection of the orientation position by the orientation sensor 8.

Also, the rate at which the push-in gasket 17 is pushed in by the piston 5 is set so that if we let V1 be the push-in rate until the separation gasket 18 reaches the bypass 21, V2 be the push-in rate at the point when the separation gasket 18 goes through the bypass 21, V3 be the push-in rate at the point when air is vented after the separation gasket 18 has gone through the bypass 21, and V4 be the push-in rate at the point when a pharmaceutical is injected after air venting, the push-in rate V2 will be lower than the push-in rate V1.

The main body case 2 is made up of a housing 22 and a distal end cap 23 on the distal end side of the housing 22. The distal end cap 23 is removably mounted to the housing 22. A window 24 for checking the volume of formulation is provided on the outer peripheral part of the distal end cap 23.

After the pharmaceutical syringe 4 has been mounted inside the pharmaceutical syringe mounting portion 3, the outer periphery of the pharmaceutical syringe 4 is covered by a syringe cover 25. The injection needle 14 is then mounted to the distal end gasket 16 from above the syringe cover 25, on the distal end side of the pharmaceutical syringe 4.

When the piston 5 pushes the push-in gasket 17 forward, the liquid pharmaceutical 20 goes through the bypass 21 and flows to the solid pharmaceutical 19 side. When the push-in gasket 17 moves farther forward, the formulation obtained by mixing the solid pharmaceutical 19 and the liquid pharmaceutical 20 flows out of the injection needle 14.

The rotation of the piston drive motor 10 is detected by an encoder 26. Consequently, the amount by which the piston 5 protrudes is detected. The solid pharmaceutical 19 and the liquid pharmaceutical 20 housed inside the pharmaceutical syringe 4 are put in at the manufacturing site of the pharmaceuticals, such as at a pharmaceutical company.

A detector switch is housed in the housing 22 of the main body case 2. More specifically, a distal end cap detector switch 28 is disposed at the rear end of a control rod 27 provided around the outer periphery of the pharmaceutical syringe mounting portion 3. Consequently, when the distal end cap 23 is mounted to the distal end of the housing 22, the control rod 27 is pushed rearward, and the distal end cap detector switch 28 detects that the distal end cap 23 has been mounted.

A control rod 29 is disposed inside the pharmaceutical syringe mounting portion 3. When the control rod 29 is pushed rearward by the syringe cover 25, a syringe cover detector switch 30 detects that the syringe cover 25 has been mounted.

In this embodiment, the substrate 7a is disposed parallel to the drive direction of the piston 5, but may instead be installed perpendicular to the drive direction of the piston 5.

Control buttons are provided to the outer periphery of the housing 22 of the main body case 2. More specifically, a power button 31 is provided to the rear end of the housing 22. A mix button 32, a pharmaceutical injection button 33, and an end button 34 are provided to the outer periphery of the housing 22 near a display section 35.

Figure 3:
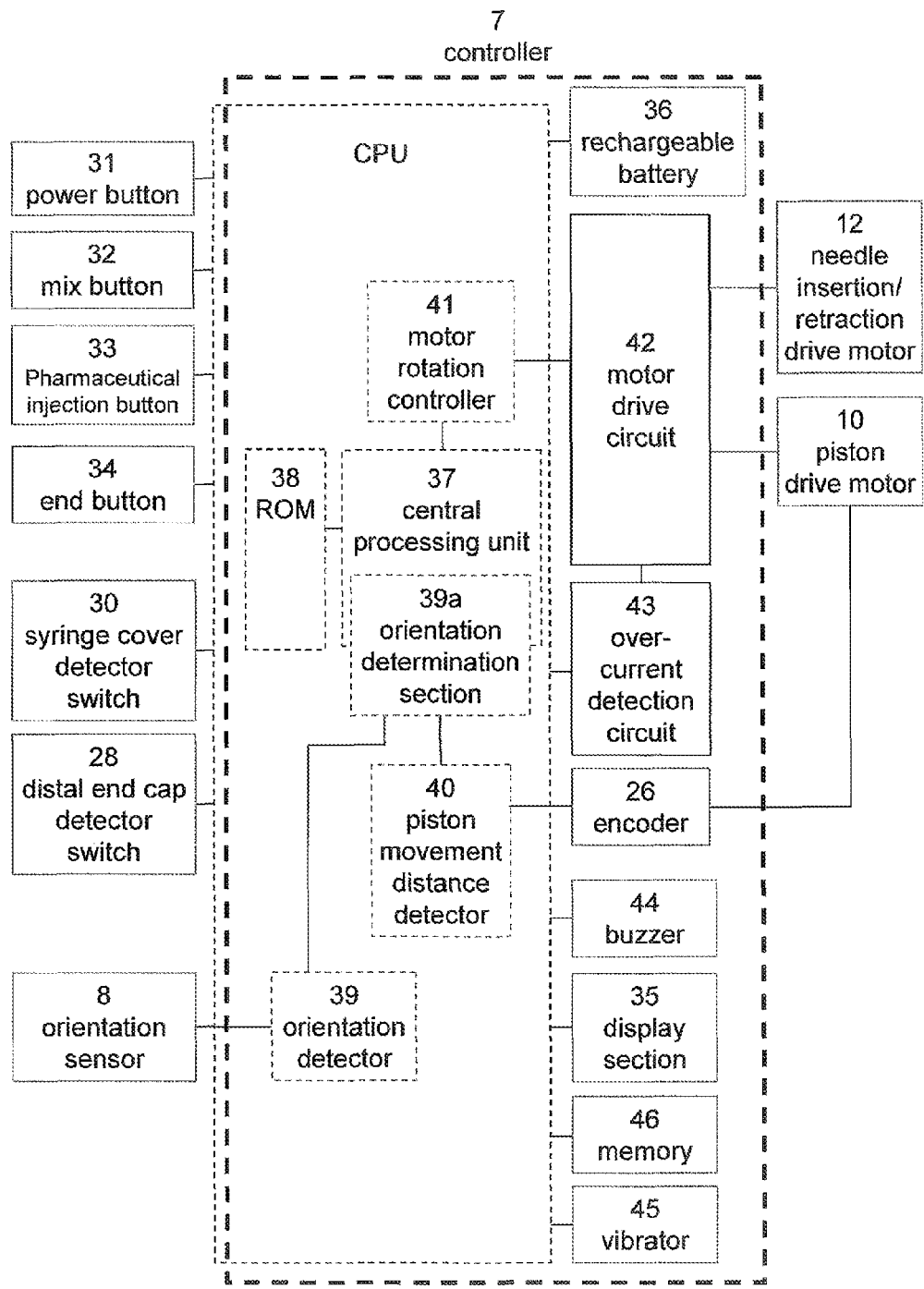
FIG. 3 is a simplified block diagram of the electrical configuration of the pharmaceutical injection device in FIG. 1.

FIG. 3 is a simplified block diagram of the electrical configuration.

The controller 7 is made up of a microprocessor and electrical drive parts. Electricity is supplied from a rechargeable battery 36 (shown in FIG. 3) to the controller 7 and other electrical drive parts.

A central processing unit 37 is provided to the microprocessor of the controller 7. The central processing unit 37 issues commands so that operational control is performed, and various programs are written to a ROM 38. An orientation detector 39, a piston movement distance detector 40, and a motor rotation controller 41 are included in the microprocessor.

The orientation detector 39 is connected to an orientation determination section 39a and the orientation sensor 8, and converts the orientation detection result from the orientation sensor 8 into information for determining the orientation at the orientation determination section 39a.

The orientation determination section 39a performs operational control according to the orientation of the pharmaceutical injection device, such as using the orientation information obtained from the orientation detector 39 to compare the inclination detected by the orientation sensor 8 with a set value, determine whether or not to drive the piston drive motor 10, etc.

The piston movement distance detector 40 is connected to the encoder 26, and detects the movement distance of the piston 5 by detecting the rotation of the piston drive motor 10.

The motor rotation controller 41 is connected to a motor drive circuit 42, and when the value detected by the piston movement distance detector 40 reaches a set value, the motor rotation controller 41 controls the motor drive circuit 42 to control the movement speed of the piston 5.

The piston drive motor 10 and the needle insertion/retraction drive motor 12 are connected to the motor drive circuit 42. The motor drive circuit 42 is connected to an over-current detection circuit 43.

The motor drive circuit 42 is controlled by the motor rotation controller 41, and drives the piston drive motor 10 and the needle insertion/retraction drive motor 12.

The over-current detection circuit 43 is a circuit that detects the amount of current from the motor drive circuit 42, and detects motor problems.

The controller 7 is also connected to a buzzer 44 and a vibrator 45 for issuing a warning so as to alert the user to the status of the unit. The controller 7 is also connected to the display section 35, which displays warnings and information for operating the unit, and to a memory 46 for recording various kinds of data.

Next, the operational control of the pharmaceutical injection device will now be described through reference to the operational flowchart shown in FIG. 4.

Figure 4:
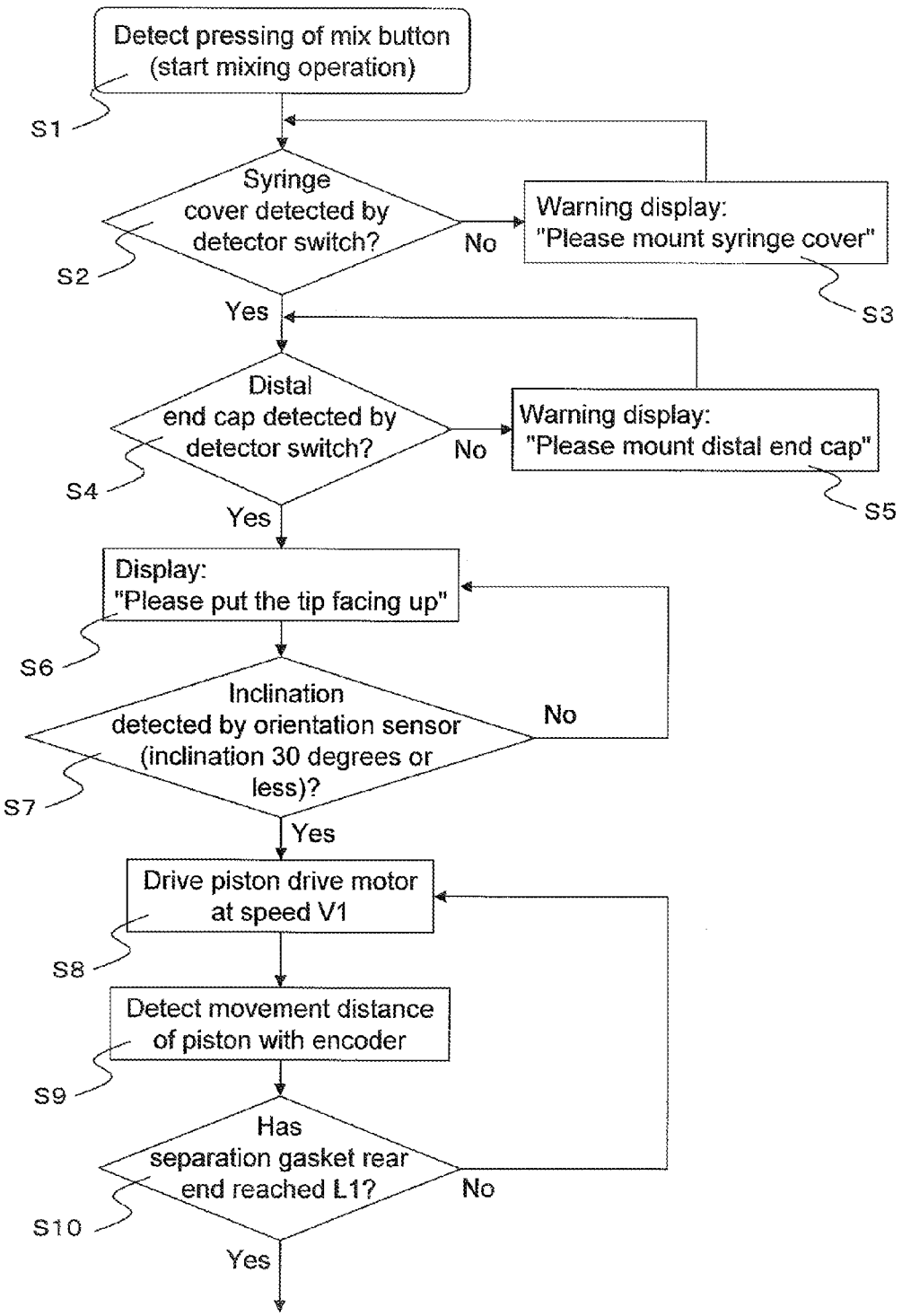
FIG. 4 is a flowchart of the operational control of the pharmaceutical injection device in FIG. 1.

As shown in FIG. 4, first, in S1 the user presses the mix button 32 (see FIG. 1).

Then, in S2 the syringe cover detector switch 30 detects whether or not the syringe cover 25 has been mounted. If the syringe cover 25 has not been mounted, in S3 a warning display prompting mounting ("Please mount syringe cover") is given on the display section 35 (see FIG. 1).

Meanwhile, if the syringe cover detector switch 30 detects the mounting of the syringe cover 25 in S2, then in S4 the distal end cap detector switch 28 detects whether or not the distal end cap 23 has been mounted. If the distal end cap 23 has not been mounted, then in S5 a warning display prompting mounting ("Please mount distal end cap") given on the display section 35.

Specifically, in this embodiment, in S2 and S4, if neither the syringe cover 25 nor the distal end cap 23 has been mounted, the flow does not proceed to the subsequent operation.

If the mounting of the syringe cover 25 and the distal end cap 23 is detected, in S6 a display of "Please put the tip facing up" is left on the display section 35 for a specific length of time.

In S7, the orientation sensor 8 detects the inclination of the pharmaceutical injection device.

Hereinafter, the term inclination is defined such that when the distal end cap 23 is disposed so as to be perpendicular to the horizontal plane, the perpendicular direction is zero degrees. Here, if the inclination exceeds the set value, operation is halted until the inclination falls back to within the set value, and operation is restarted once the inclination has been within the set value for a specific length of time. When leakage from the injection needle 14 is taken into account, it is preferable for the inclination at which operation can be sustained to be from 30 to 45 degrees. 30 degrees is set as a threshold in this embodiment.

Figure 7:
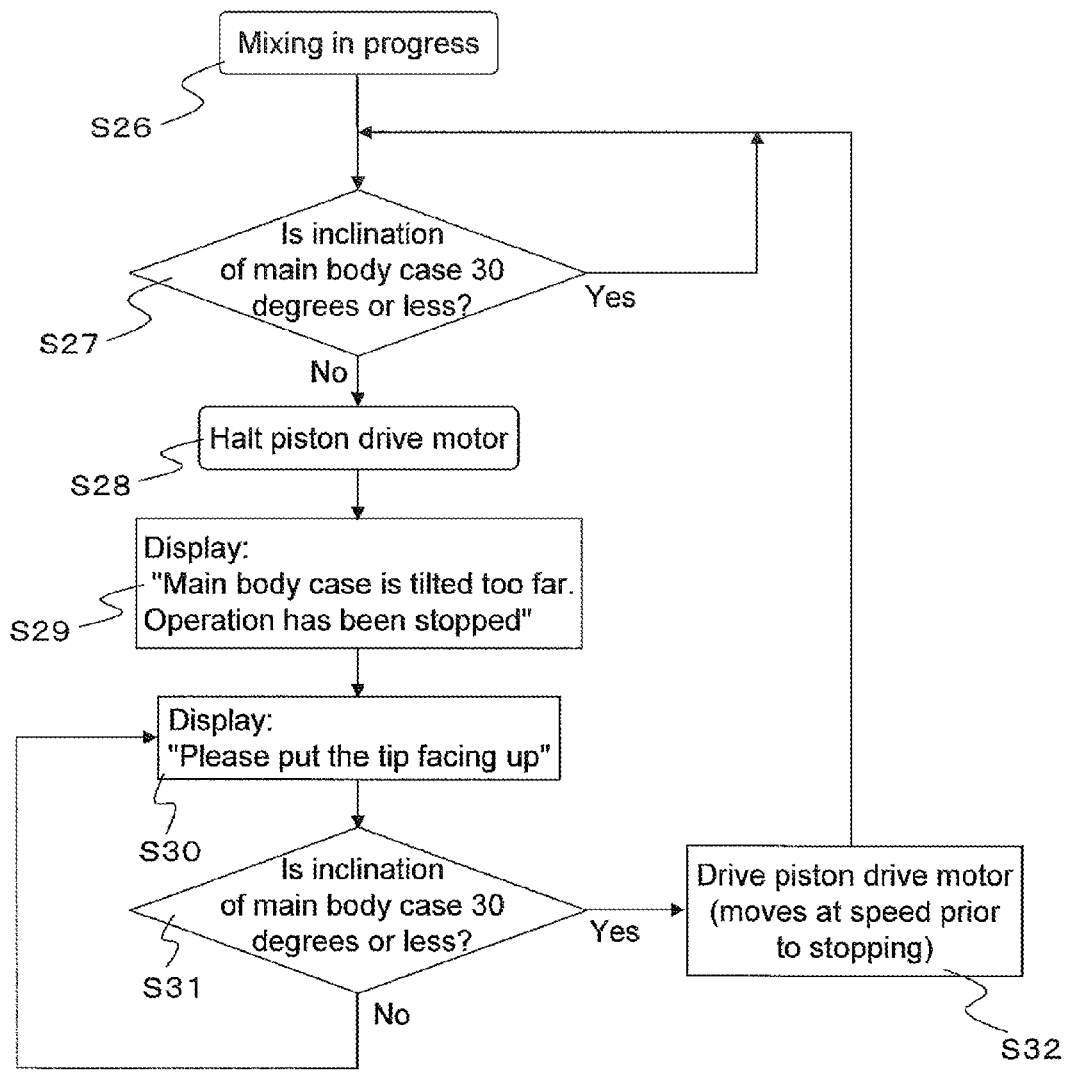
FIG. 7 is a flowchart of the operational control of the pharmaceutical injection device in FIG. 1.

During the operation in steps S7 and beyond, as shown in FIG. 7, detection of the inclination continues to be detected (S26 in FIG. 7) by the orientation sensor 8 while the rear end position of the separation gasket 18 is between a position L1 and a position L3 (see FIG. 8). When the inclination of the main body case 2 exceeds 30 degrees (S27 in FIG. 7), the piston drive motor 10 is halted (S28 in FIG. 7), and the display section 35 gives warning displays of "Main body case is tilted too far. Operation has been stopped" (S29 in FIG. 7) and "Please put the tip facing up" (S30 in FIG. 7). This prompts the user to adjust the inclination of the main body case 2 to 30 degrees or less.

In S31 shown in FIG. 7, it is confirmed that the inclination of the main body case 2 is over 30 degrees by a loop with S30, and if the inclination is found to be 30 degrees or less, in S32 the operation that was in progress prior to the stoppage is restarted, the flow returns to S8 in FIG. 4, and the detection of inclination is continued.

Figure 9B:
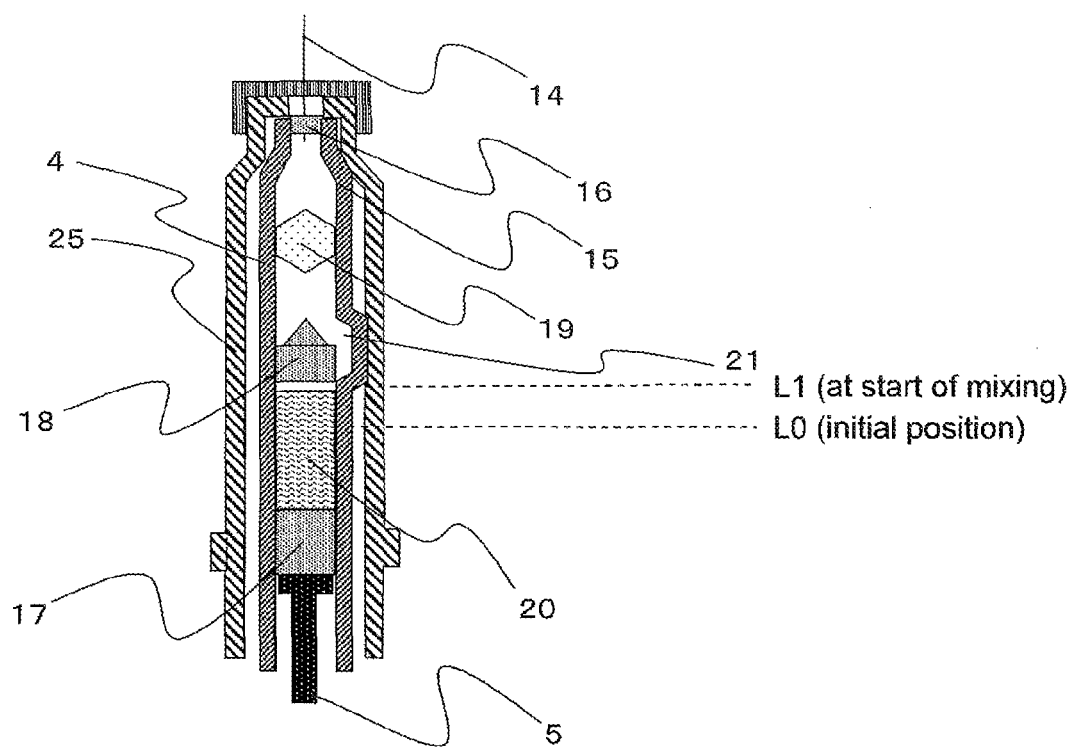
FIG. 9B is a syringe cross section of the operating state of the piston in the pharmaceutical injection device in FIG. 1.

In S8 in FIG. 4, as shown in FIG. 9A, the piston drive motor 10 is driven at the push-in rate V1 from the initial state prior to the mixing operation, and in S9 in FIG. 4, the movement distance of the piston 5 is calculated by the encoder 26 during drive of the piston 5. Next, in S10, the piston drive motor 10 is driven at the push-in rate V1 until the rear end of the separation gasket 18 goes from the initial position L0 to the position L1 in FIG. 9B. As shown in FIG. 9B, the position L1 indicates the position where the rear end of the separation gasket 18 touches the bypass 21. Position information about the position L1 is stored in the memory 46.

Figure 5:
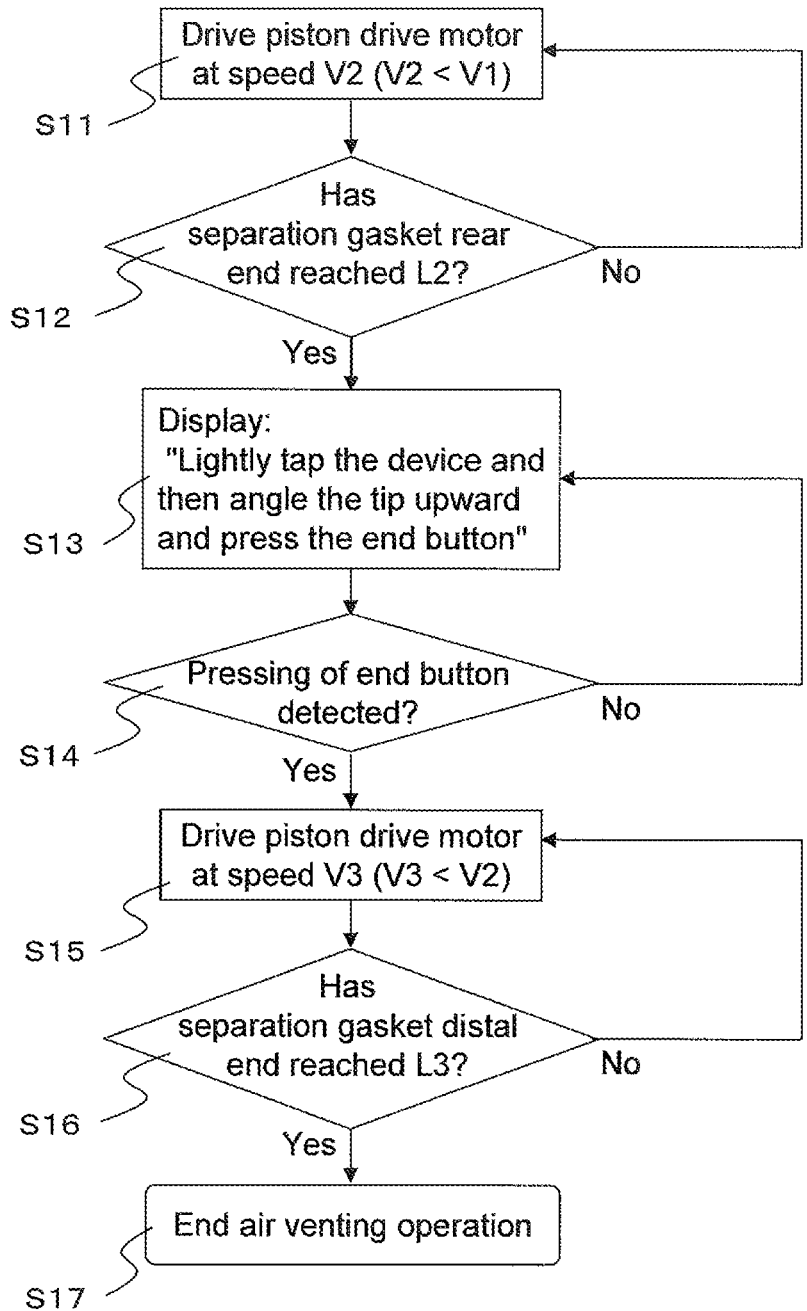
FIG. 5 is a flowchart of the operational control of the pharmaceutical injection device in FIG. 1.

When the rear end of the separation gasket 18 reaches the position L1, the mixing operation commences, and in S11 in FIG. 5, the push-in rate of the separation gasket by the piston drive motor 10 is V2, which is lower than the push-in rate V1 (V2<V1).

Figure 9C:
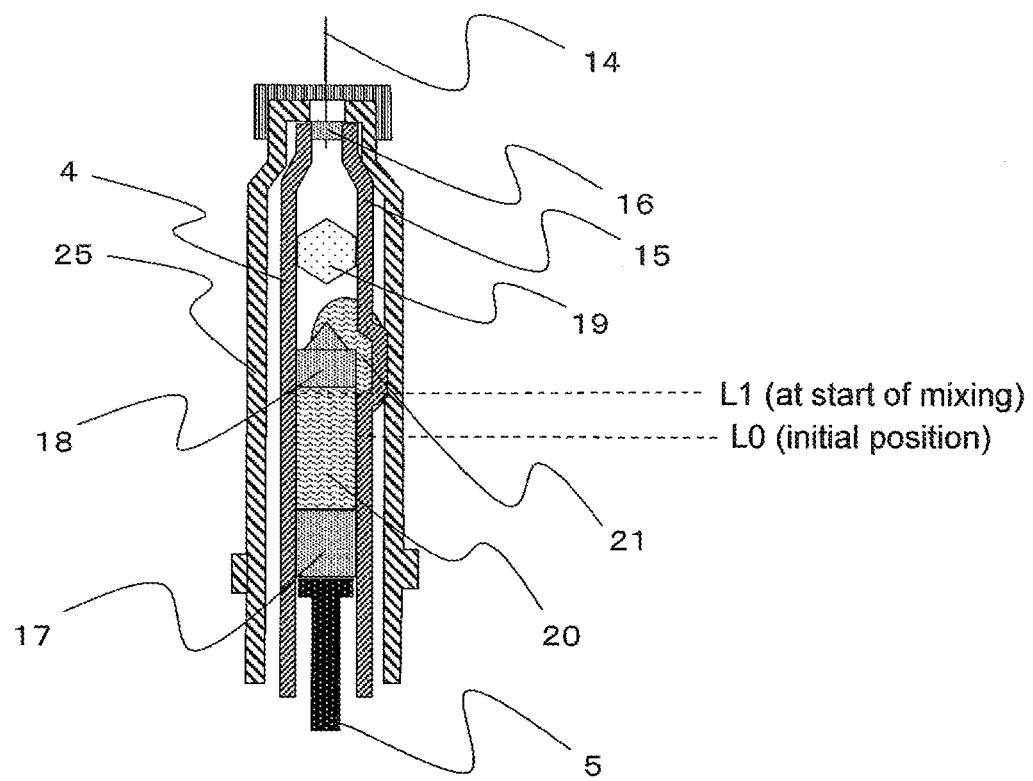
FIG. 9C is a syringe cross section of the operating state of the piston in the pharmaceutical injection device in FIG. 1.

In FIG. 9C, when the rear end of the separation gasket 18 starts to pass through the bypass 21, the liquid pharmaceutical 20 begins to flow through the bypass 21 to the solid pharmaceutical 19 side.

Figure 9D:
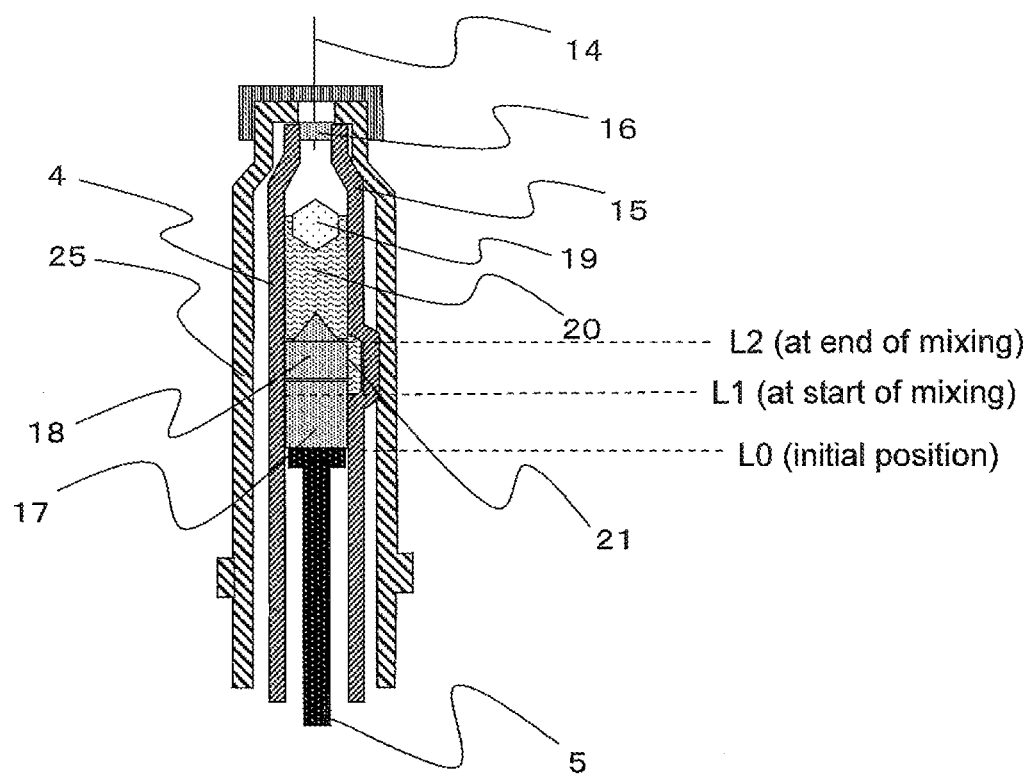
FIG. 9D is a syringe cross section of the operating state of the piston in the pharmaceutical injection device in FIG. 1.

In S12, the piston drive motor 10 is driven at the push-in rate V2 until the rear end of the separation gasket 18 reaches the position L2 in FIG. 9D, that is, until the rear end of the separation gasket 18 reaches the position where it is in contact with the push-in gasket 17 (at the completion of the mixing operation). Position information about the position L2 is stored in the memory 46.

In this embodiment, because the push-in rate V2 of the separation gasket 18 by the piston drive motor 10 is set lower than the push-in rate V1, it is less likely that there will be a sudden surge in pressure on the solid pharmaceutical 19 side when the liquid pharmaceutical 20 passes through the bypass 21. As a result, this prevents some of the liquid pharmaceutical from squirting out of the distal end of the injection needle 14 mounted to the distal end gasket 16 of the cylinder 15, or from overflowing more than necessary. Thus, liquid leakage from the distal end gasket side can be reduced during pharmaceutical mixing.

As shown in FIG. 9D, when the distal end position of the separation gasket 18 reaches the position L2, the display section 35 displays "Lightly tap the device and then angle the tip upward and press the end button" as shown in S13 in FIG. 5, and the operation of the piston drive motor 10 is temporarily halted.

Next, in S14 in FIG. 5, air venting starts when the end button 34 is pressed, and the inclination is detected by the orientation sensor 8 while the push-in rate V3 of the separation gasket 18 by the piston drive motor 10 is set to be lower than the push-in rate V1 (V3<V1). Preferably, the push-in rate V3 is set to be lower than the push-in rate V2 (V3<V2).

Here, since liquid is most apt to leak from the distal end of the injection needle 14, the speed at which the piston 5 is moved is further lowered (S15 in FIG. 5), which prevents as much as possible the leakage of liquid from the distal end of the injection needle 14.

Figure 9E:
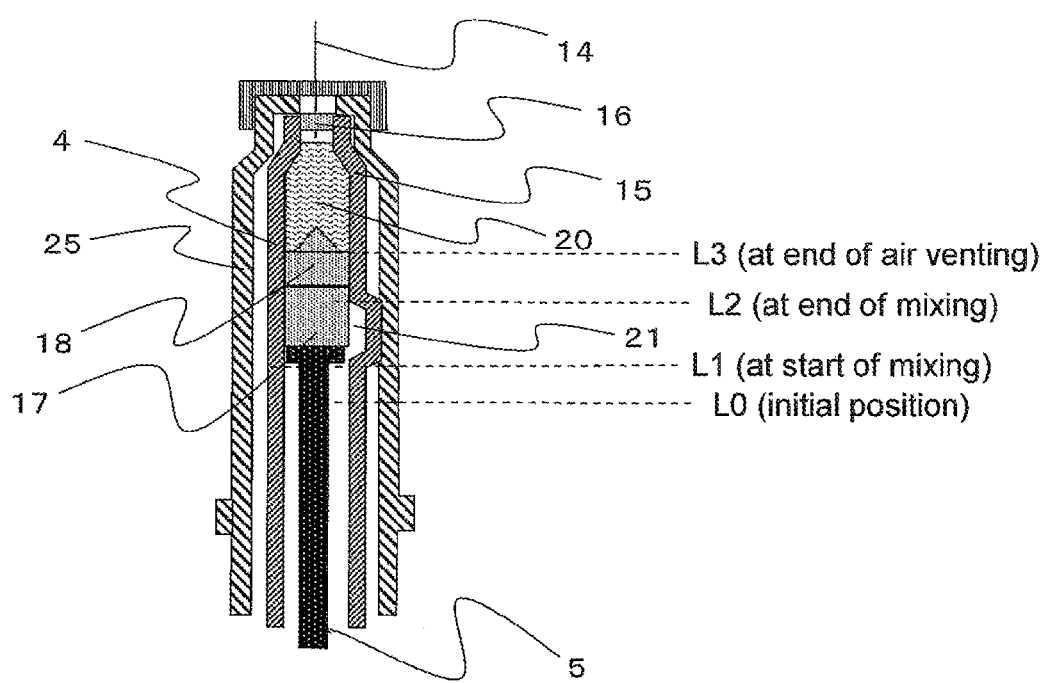
FIG. 9E is a syringe cross section of the operating state of the piston in the pharmaceutical injection device in FIG. 1.

In S16 in FIG. 5, the piston drive motor 10 is driven at the push-in rate V3 until the distal end position of the separation gasket 18 arrives at the position L3. As shown in FIG. 9E, the position L3 indicates the position after the separation gasket 18 and the push-in gasket 17 have passed through the bypass 21 in a state of being in contact with each other. Position information about the position L3 is stored in the memory 46.

As shown in S17 in FIG. 5, the air vent operation is ended when the distal end position of the separation gasket 18 reaches the position L3.

Figure 6:
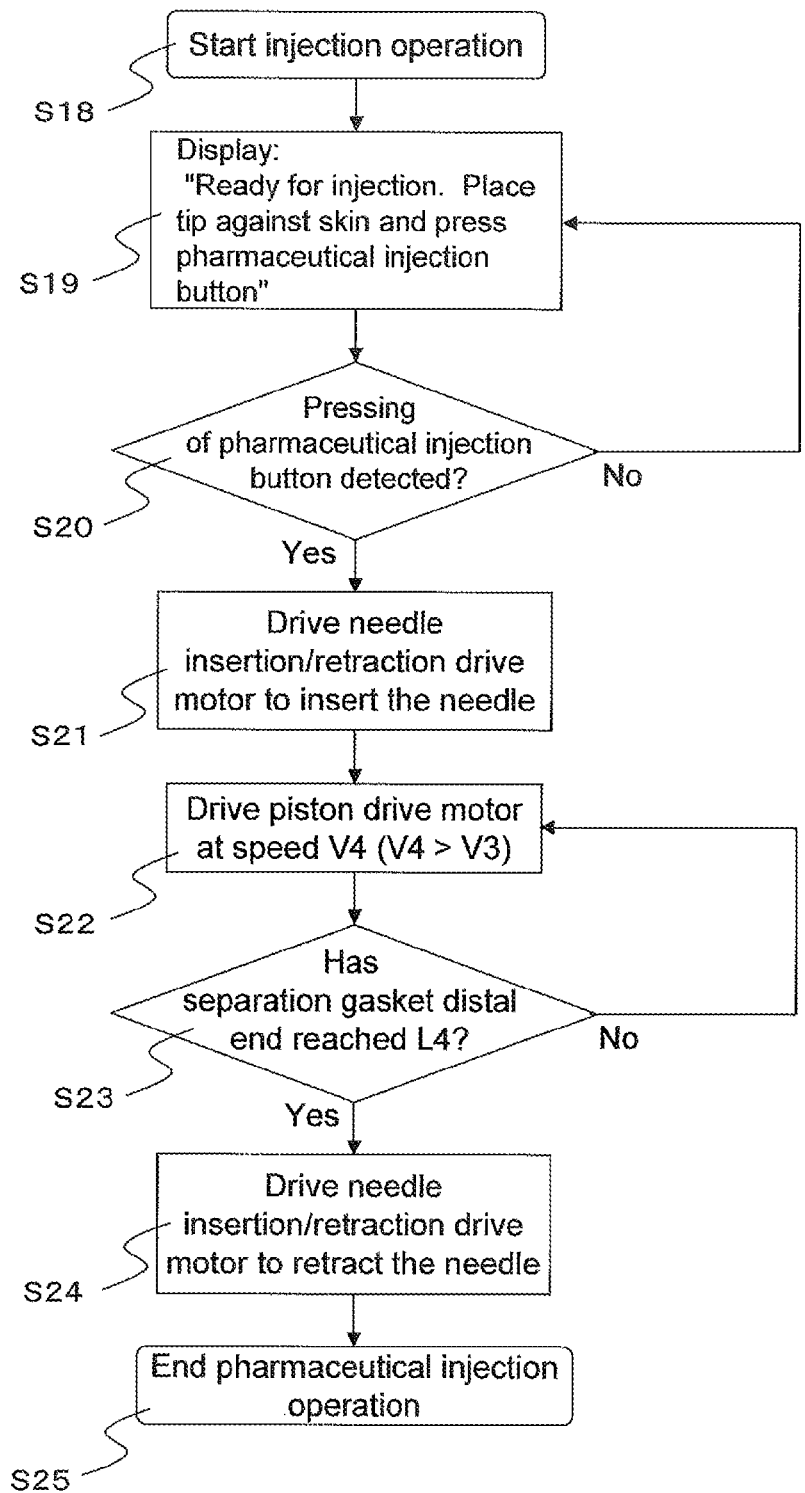
FIG. 6 is a flowchart of the operational control of the pharmaceutical injection device in FIG. 1.

As shown in FIG. 6, in S18, the pharmaceutical injection operation is then commenced.

Next, in S19, a message of "Ready for injection. Place tip against skin and press pharmaceutical injection button" is displayed on the display section 35, and the operation of the piston drive motor 10 is temporarily halted.

In S20, it is determined whether or not the pharmaceutical injection button 33 has been pressed.

Here, when the pharmaceutical injection button 33 is pressed, the operation of piercing the skin is commenced in S21. This operation entails driving the needle insertion/retraction drive motor 12. This piercing operation refers to an operation in which the pharmaceutical syringe mounting portion 3 is moved to the injection needle extension/retraction opening 1 side by drive of the needle insertion/retraction drive motor 12, and the injection needle 14 is made to protrude from the injection needle extension/retraction opening 1.

At this point, since the injection needle extension/retraction opening 1 is pressed against the part of the body where the injection is to be made, the injection needle 14 is moved toward the body, the injection needle 14 pierces the skin, and the preparatory operation prior to pharmaceutical injection (the piercing operation) is concluded.

Next, the pharmaceutical injection operation is commenced in S22.

The push-in rate V4 of the separation gasket 18 by the piston drive motor 10 during the pharmaceutical injection operation is controlled to be higher than the push-in rate V3 (V4>V3). This is because liquid is less likely to leak from the distal end of the injection needle in this state, so the speed at which the piston 5 is moved is higher.

Figure 9F:
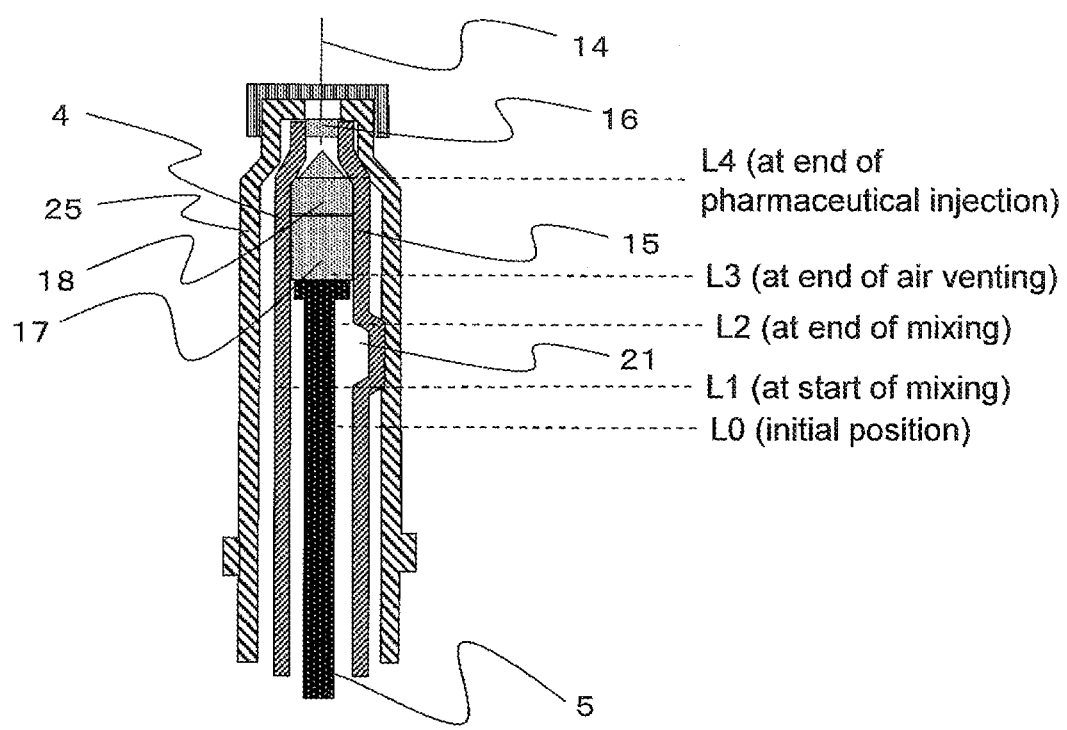
FIG. 9F is a syringe cross section of the operating state of the piston in the pharmaceutical injection device in FIG. 1.

In S23, the piston drive motor 10 is driven at the push-in rate V4 until the distal end position of the separation gasket 18 reaches the position L4. As shown in FIG. 9F, the position L4 indicates the position at which the separation gasket 18 reaches the distal end of the pharmaceutical syringe 4. Position information about the position L4 is stored in the memory 46.

Finally, when the distal end position of the separation gasket 18 reaches the position L4 in S23, the needle retraction operation is commenced in S24. In the needle retraction operation, the piston drive motor 10 is halted and the needle insertion/retraction drive motor 12 is moved, and the drive of the needle insertion/retraction drive motor 12 moves the pharmaceutical syringe mounting portion 3 to the rear end side, which causes the injection needle 14 to be housed inside the injection needle extension/retraction opening 1.

After this, in S25 when the pharmaceutical syringe mounting portion 3 reaches the initial point prior to the needle insertion operation, the needle retraction operation is stopped, and the operation of injecting the pharmaceutical into the body is concluded.

FIG. 8 is a graph of the operating state during mixing in the pharmaceutical injection device in this embodiment. The vertical axis is the voltage (value) of a piston speed control signal for driving the piston drive motor 10, and the horizontal axis is the rear end position or distal end position of the separation gasket 18.

The push-in rate is proportional to the voltage value of the piston speed control signal (for example, V1 and V4 are 1.0 volt, V2 is 0.8 volt, and V3 is 0.7 volt).

The graph in FIG. 8 is just an example, though, and the waiting time for operation by the user can be assigned as needed between V2 and V3 and between V3 and V4. In this case, the mixing operation can be temporarily halted and the various push-in rates set to zero.

As discussed above, with the pharmaceutical injection device in this embodiment, during the pharmaceutical mixing operation the push-in rate V2 at which the separation gasket 18 passes through the bypass 21 is controlled to be lower than the push-in rate V1 when the separation gasket 18 is pushed in until it comes into contact with the bypass 21.

Consequently, the liquid pharmaceutical 20 can flow gently through the bypass 21 to the solid pharmaceutical 19 side. As a result, leakage of liquid from the distal end gasket 16 side can be reduced during pharmaceutical mixing.

Therefore, when the user operates the pharmaceutical injection device, the pharmaceutical will not splash onto anything in the surrounding area, the area can be kept clean, and the automatic pharmaceutical mixing operation can be carried out simply, safely, and properly.

INDUSTRIAL APPLICABILITY

The pharmaceutical injection device of the present invention reduces liquid leakage during pharmaceutical mixing, so it has the effect of allowing the pharmaceutical mixing operation to be carried out properly, and therefore this device is expected to find widespread use in fields such as pharmaceutical injection devices that require a pharmaceutical mixing operation.

REFERENCE SIGNS LIST 1 injection needle extension/retraction opening
2 main body case
3 pharmaceutical syringe mounting portion
4 pharmaceutical syringe
5 piston
6 drive mechanism
7 controller
7a substrate
8 orientation sensor
9 bolt
10 piston drive motor
11 female thread
12 needle insertion/retraction drive motor
13 bolt
14 injection needle
15 cylinder
16 distal end gasket
17 push-in gasket
18 separation gasket
19 solid pharmaceutical
20 liquid pharmaceutical
21 bypass
22 housing
23 distal end cap
24 window
25 syringe cover
26 encoder
27 control rod
28 distal end cap detector switch
29 control rod
30 syringe cover detector switch
31 power button
32 mix button
33 pharmaceutical injection button
34 end button
35 display section
36 rechargeable battery
37 central processing unit
38 ROM
39 orientation detector
39a orientation determination section
40 piston movement distance detector
41 motor rotation controller
42 motor drive circuit
43 over-current detection circuit
44 buzzer
45 vibrator
46 memory
47 movement axis

The invention claimed is:

1. A pharmaceutical injection device, comprising:
a main body case having an opening from which an injection needle retractably protrudes;
a pharmaceutical syringe mounting portion that is provided within the main body case and to which a pharmaceutical syringe is removably mounted;
a piston that is provided movably with respect to the pharmaceutical syringe;
a drive mechanism that drives the piston;
a controller that is electrically connected to the drive mechanism; and
an orientation sensor that is electrically connected to the controller,
wherein the pharmaceutical syringe has a cylinder, a distal end gasket provided on a distal end side within the cylinder, a push-in gasket provided on a rear end side within the cylinder, a separation gasket provided in a middle within the cylinder, a solid pharmaceutical housed in the cylinder between the distal end gasket and the separation gasket, a liquid pharmaceutical housed in the cylinder between the push-in gasket and the separation gasket, and a bypass that sticks out in the outer peripheral direction of the cylinder at a portion of the cylinder between the distal end gasket and the separation gasket,
the controller uses the drive mechanism to push the push-in gasket to the distal end gasket side with the piston after detection of an orientation position by the orientation sensor, and
the rate at which the push-in gasket is pushed in by the piston is set so that a push-in rate V2 will be lower than a push-in rate V1, a push-in rate V3 will be lower than the push-in rate V1 and a push-in rate V4 will be higher than the push-in rate V3, where V1 is the push-in rate until the separation gasket reaches the bypass, V2 is the push-in rate at the point when the separation gasket goes through the bypass, V3 is the push-in rate at the point when air is vented after the separation gasket has gone through the bypass, and V4 is the push-in rate at the point when a pharmaceutical is injected after air venting.

2. The pharmaceutical injection device according to claim 1,
wherein the orientation sensor is mounted on a substrate having the controller, and
the substrate is installed so as to be either parallel or perpendicular to the drive direction of the piston.

3. The pharmaceutical injection device according to claim 1,
wherein the controller stops the piston from moving to the opening side when the orientation sensor has detected inclination at or above a set value.

* * * * *